United States Patent [19]
Taymor-Luria

[11] Patent Number: 5,415,657
[45] Date of Patent: May 16, 1995

[54] PERCUTANEOUS VASCULAR SEALING METHOD

[76] Inventor: Howard Taymor-Luria, 34 Cove Rd., Belvedere, Calif. 94920

[21] Appl. No.: 959,337

[22] Filed: Oct. 13, 1992

[51] Int. Cl.⁶ ............................................. A61B 17/38
[52] U.S. Cl. .......................................... 606/49; 606/40; 606/27; 128/898
[58] Field of Search ................ 606/17, 40, 27–31, 606/41, 49, 213, 215, 216; 128/898

[56] References Cited

U.S. PATENT DOCUMENTS

| | | | |
|---|---|---|---|
| 3,176,114 | 3/1965 | Kneisley | 606/27 |
| 3,613,682 | 10/1971 | Naylor | |
| 3,699,967 | 10/1972 | Anderson | |
| 3,801,800 | 4/1974 | Newton | |
| 3,874,388 | 4/1975 | King et al. | 606/213 |
| 3,963,030 | 6/1976 | Newton | |
| 4,424,833 | 1/1984 | Spector et al. | |
| 4,929,246 | 5/1990 | Sinofsky | |
| 5,057,105 | 10/1991 | Malone et al. | 606/31 |
| 5,108,421 | 4/1992 | Fowler | 606/213 |
| 5,156,613 | 10/1992 | Sawyer | 606/8 |
| 5,158,561 | 10/1992 | Rydell et al. | 606/29 |
| 5,188,634 | 2/1993 | Hussein et al. | 606/14 |
| 5,226,908 | 7/1993 | Yoon | 606/28 |

FOREIGN PATENT DOCUMENTS 3838840 5/1990 Germany ........................... 606/31

OTHER PUBLICATIONS

Vasoseal by Datascope Corporation of Montvale, N.J.

Primary Examiner—Stephen C. Pellegrino
Attorney, Agent, or Firm—Flehr, Hohbach, Test, Albritton & Herbert

[57] ABSTRACT

A percutaneous vascular sealing assembly (30) for sealing a puncture opening (17) in a blood vessel (16) following an invasive medical procedure. The sealing assembly includes an elongated tubular shaft (32) having a distal end (36) carrying an electrosurgical sealing assembly (34). An energy source assembly (38) is connected to the sealing assembly (34) to enable hemostasis of the puncture site. An associated method for percutaneous positioning of the sealing assembly (30) in substantially direct engagement with the blood vessel (16) at the puncture (17) following a medical procedure is provided. The method includes the steps of aligning guide means (12,28) in axial alignment with the puncture, mounting the sealing assembly (30) for movement along the guide means (12,28), and moving at least one of the sealing assembly (30) and guide means (12,28) until a transverse shoulder (20,36) encounters increased resistance to movement toward the blood vessel (16) by reason of engaging the exterior surface (40) of the blood vessel (16).

20 Claims, 9 Drawing Sheets

PERCUTANEOUS VASCULAR SEALING METHOD

TECHNICAL FIELD

This invention relates to a novel apparatus and method for percutaneously sealing a puncture in a blood vessel wall following an invasive medical procedure. More specifically, this invention relates to a vascular sealing apparatus and method of employing electrosurgical sealing to rapidly seal a puncture site in a blood vessel wall following removal of a sheath assembly from the blood vessel wall.

BACKGROUND ART

Percutaneous vascular procedures form an integral portion of radiological and cardiological medical practices. It is estimated that approximately one million invasive procedures are performed each year, including peripheral and carotid angiograms, catheterizations, angioplasties, and atherectomies. In such procedures, a puncture opening distending sheath assembly is introduced into a blood vessel, for example, the femoral artery in a patient's leg. A medical device, such as a catheter, is introduced through the sheath assembly and then advanced through the blood vessel to the coronary, or other operative, region.

The majority of these invasive procedures are performed using the Seldinger technique to gain percutaneous vascular access to the blood vessel. According to this technique, the blood vessel, which in the case of the femoral artery is typically located one half inch or more beneath the skin, is punctured through the overlying tissue by a hollow-core needle. A guide wire then is threaded through the hollow core of the needle and into the artery. The needle is subsequently withdrawn from the artery, while the guide wire is maintained in place. Next, a blood vessel wall dilator and a thin-walled, tubular, puncture-distending sheath are introduced into the artery with the blood vessel dilator inside the sheath. The dilator and the sheath are moved along the guide wire and through the puncture site to an intravascular position. The dilator extends outwardly of the end of the sheath and gradually distends the puncture opening as it is advanced into the blood vessel wall until the opening will receive the sheath. The guide wire and the dilator are then withdrawn from the artery while the distending sheath assembly is left in place. Prior to the introduction of medical devices into the artery, anti-coagulants are administered to prevent blood clotting. Finally, a catheter, or other medical device, may be inserted through the sheath assembly to perform the necessary invasive procedure.

Following the medical procedure, the medical device is removed from the sheath assembly and the sheath assembly is removed from the puncture site in the artery. The time which elapses prior to sheath removal varies considerably depending on the procedure being performed. Other factors which govern the amount of lapsed time prior to sheath removal include the size of the sheath employed, the amount of anti-coagulant administered, and the patient's clinical circumstance. The combinations of all of these factors often results in a relatively long waiting period between the completion of the procedure and the removal of the sheath assembly, which adds to patient discomfort and anxiety.

Once the sheath assembly is removed from the artery, it has been customary to obtain hemostasis at the puncture site by applying indirect, external pressure to the femoral artery and vein. This is usually accomplished manually by a nurse or physician, or with the aid of a mechanical clamp, employed by the nurse or physician. Often, compression must be applied for ten to thirty minutes before sufficient clotting occurs. Once hemostasis is achieved, a pressure dressing is typically applied to the patient's leg for several hours. In addition, six to twelve hours of bed rest is typically required to reduce the risk and incidence of hematoma formation.

Although manual compression has proven successful in obtaining hemostasis over the years, there are numerous problems and disadvantages associated with this method. The procedure is extremely time-consuming from both a patient and a physician standpoint and further is an inefficient use of the medical professional staff. Moreover, manual and mechanical compression are extremely uncomfortable to the patient and frequently is associated with vaso-vagal episodes. In addition, bruise or hematoma formation at the entry site often occurs as a result of internal bleeding of the punctured artery before clotting blocks the puncture. The possibility of psuedoaneurysm formation also exists with the manual compression technique of achieving hemostasis.

In response to some of the problems associated with manual compression, a percutaneous apparatus and method for forming a vascular seal has been developed and commercially exploited under the trade name VASOSEAL by Datascope Corporation of Montvale, N.J. According to this method, a measuring device is used to calculate the distance between the skin surface and the operative vessel wall at the beginning of the catheterization procedure. Then, when the invasive procedure is completed and the medical device and distending sheath assembly have been withdrawn, an applicator is inserted through the patient's skin and overlying tissue down the passageway formerly receiving the sheath assembly to the previously measured depth. The applicator is actuated to deliver a volume of collagen to the puncture site. The collagen utilized by the Datascope apparatus and method is made of resorbable natural fibers and attracts and activates platelets to form a coagulum at the vessel surface, sealing the surface of the artery. Such a collagen seal is typically formed in less than five minutes, involving significantly less time and labor than that required by the manual compression technique. The collagen itself applies a discrete pressure against the blood vessel wall, much like finger pressure delivered to a skin wound, but some direct, external pressure still must be applied to the entry site once the collagen has been injected.

Although the Datascope method significantly reduces the amount of manual compression required, the necessary manual compression remains an inefficient use of a physician's time. Moreover, the Datascope method involves some risk associated with deploying collagen intravascularly, or only at an approximate location along the vessel wall, rather than at a specific, identifiable position on the vessel wall surface. For example, manipulation of the blood vessel during the catheterization procedure may cause the blood vessel to shift, reducing the accuracy of the measurement taken before the catheterization procedure. Intravascular deposition of collagen can produce an embolism and possible ischemia within the patient's leg, which may require further medical intervention. Deposits of collagen remote of the puncture site may be ineffective in establishing hemostasis.

Another method for closing and sealing an artery following removal of a catheter is disclosed in U.S. Pat. No. 4,929,246 to Sinofsky. This method involves applying laser energy to a puncture site to thermally weld the artery. In a preferred embodiment, a sheath assembly is withdrawn to a spaced distance from the artery and puncture site and a tube having a balloon at its distal end is advanced through the sheath assembly. The balloon is then inflated to apply pressure to the exterior wall of the artery, temporarily blocking blood flow from the puncture. The tube also carries an optical fiber which extends into the balloon and directs a beam of laser energy against the interior of the balloon. The laser energy indirectly thermally welds the artery wall. Creating a vascular seal with a laser as disclosed in the Sinofsky patent, however, is a costly, somewhat indirect and a complex solution to hemostasis.

It also is widely known in the medical field to heat weld exposed blood vessels during an operative procedure or to electrosurgically coagulate escaping blood to effect vascular sealing. For example, laser energy has been routinely directly employed to provide the necessary thermal energy to weld brachial arteries during a Sones procedure. In addition, both electro-cautery and electro-coagulation have been used to seal exposed small blood vessels under direct observation during operative procedures. It is believed that such electro-surgical procedures have not previously been employed to effect rapid percutaneous vascular sealing of unseen blood vessels following an invasive medical procedure.

The difficulties suggested in the preceding are not intended to be exhaustive but rather are among many which tend to reduce the effectiveness of and physician satisfaction with prior percutaneous vascular sealing devices. Other noteworthy problems may also exist; however, those presented above should be sufficient to demonstrate that such vascular sealing apparatus and methods appearing in the past will admit to worthwhile improvement.

Accordingly, it is therefore a general object of the invention to provide percutaneous vascular sealing apparatus and method which will obviate or minimize difficulties of the type previously described.

It is a specific object of the invention to provide a percutaneous vascular sealing apparatus and method which rapidly creates a vascular seal at a puncture site in a blood vessel wall following an invasive medical procedure.

It is another object of the invention to provide a percutaneous vascular sealing apparatus and method which enables accurate identification of an external surface of an operative blood vessel, thereby preventing accidental actuation of the sealing apparatus at an intravascular location or an ineffective remote location.

It is still another object of the invention to provide a percutaneous vascular sealing apparatus and method which reduces the amount of medical staff care necessary to achieve hemostasis following an invasive medical procedure, allows a patient to be ambulatory soon after the procedure, and, thereby, reduces the length of the hospital stay.

It is a further object of the invention to provide a percutaneous vascular sealing apparatus and method which eliminates the need for mechanical clamps to effect hemostasis and reduces the time required for pressure dressings upon completion of an invasive medical procedure.

It is yet a further object of the invention to provide a percutaneous vascular sealing apparatus and method which reduces the risk of rebleeding, hematoma formation, and psuedoaneurysms formation following an invasive medical procedure.

It is still a further object of the invention to provide a percutaneous vascular sealing apparatus and method which reduces patient pain and discomfort associated with invasive medical procedures.

It is yet another object of the invention to provide a percutaneous vascular sealing apparatus and method which is relatively inexpensive to manufacture and use, is disposable, and, thus, is practical for everyday use.

DISCLOSURE OF INVENTION

A preferred embodiment of the invention which is intended to accomplish at least some of the foregoing objects includes a vascular sealing assembly having an elongated member, most preferably an elongated tubular member, formed for temporary positioning through overlying tissue and up to and preferably into a blood vessel through a puncture opening at a puncture site in the blood vessel. The elongated member is formed for cooperative engagement with a guide device which guides the elongated member to the puncture site in the blood vessel. A sealing element is positioned on the elongated member at a location registered or indexed relative to a transversely extending, blood vessel-locating, shoulder on the elongated member for substantially direct engagement of the sealing element with an exterior surface of the blood vessel wall. An energy source is connected to the sealing element for generating energy sufficient to enable hemostasis of the puncture site, for example, by electro-cauterization or electro-coagulation.

Invasive medical procedures generally entail inserting catheters and/or other medical instruments or devices through a puncture-distending sheath which extends through overlying tissue and into an operative blood vessel through a puncture site. The puncture opening in the blood vessel wall must be sealed upon completion of the procedure. The method of the present invention provides for positioning of a vascular sealing assembly in substantially direct engagement with a blood vessel wall following such an invasive medical procedure to enable sealing of the puncture opening in the wall. The method includes the steps of (i) aligning elongated guide device with the puncture site through the tissue overlying the blood vessel, and (ii) moving at least one of the sealing assembly and the guide device relative to each other until a transversely extending shoulder, preferably the end of the sealing assembly, encounters increased resistance to movement toward the blood vessel as a result of substantially direct engagement with a wall of the blood vessel at the puncture site. A vascular seal may then be obtained by applying sufficient heat or coagulating energy to the blood vessel while the sealing assembly is maintained in substantially direct contact with the exterior surface of the blood vessel to effect hemostasis of the puncture site.

Other objects and advantages of the present invention will become apparent from the following detailed description of a preferred embodiment thereof taken in conjunction with the accompanying drawings.

BEST MODE OF CARRYING OUT THE INVENTION

Referring now to the drawings, wherein like numerals indicate like parts, FIGS. 1-5 illustrate a sequence of steps for percutaneously sealing a puncture opening in a blood vessel following an invasive medical procedure in accordance with a preferred embodiment of the method of the present invention.

Figure 1:
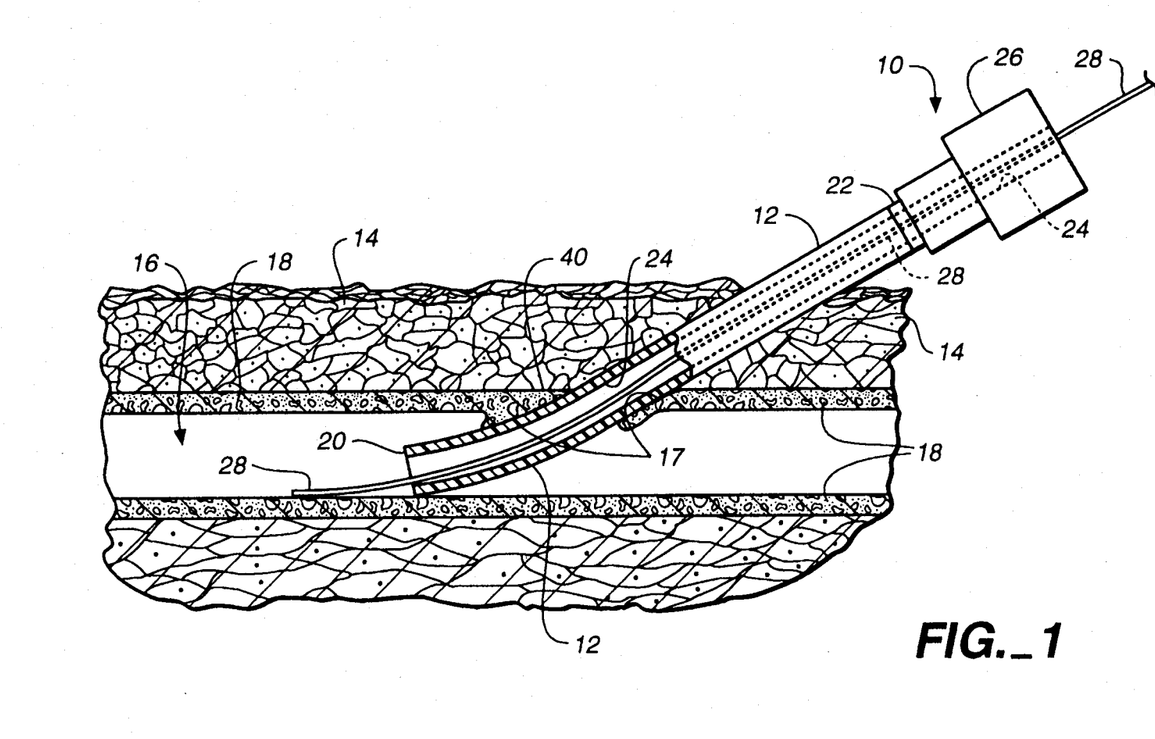
FIG. 1 is an enlarged, schematic, side elevation view of a percutaneous puncture site in a blood vessel having a puncture-distending sheath assembly and a guide wire positioned to extend from the exterior of the overlying tissue to inside the blood vessel.

In FIG. 1 there will be seen a puncture-distending sheath assembly, generally indicated 10, which includes an elongated, tubular, sheath member 12 positioned through overlying tissue 14. Sheath 12 extends into a blood vessel 16 through a puncture opening or bore 17 in blood vessel wall 18. The sheath serves as a conduit to the blood vessel during the invasive procedure, maintaining puncture opening 17 through blood vessel wall 18 distended so that medical devices can be inserted through assembly 10 into blood vessel 16.

The diameter of sheath 12 may range from approximately 5 French to 14 French, depending on the particular procedure to be performed, and inserting sheath 12 into blood vessel 16 creates a similarly sized puncture opening 17 through vessel wall 18. Placement of sheath 12 through tissue 14 and vessel wall 18, as shown in FIG. 1, is most typically accomplished using the Seldinger technique, described briefly above. The invasive medical procedures may include peripheral and carotid angiograms, catheterizations, angioplasties, and atherectomies.

Sheath member 12 has an indwelling or annular distal end 20, an exposed end 22, and a bore or lumen 24 which provides a conduit or pathway for medical devices and instruments into blood vessel 16. During catheterization procedures, for example, a catheter may be inserted through lumen 24 of sheath 12 to be positioned in blood vessel 16, normally the femoral artery, and then advanced through the blood vessel to the treatment site. Sheath assembly 10 also typically includes a port assembly 26, for example, of the type set forth in U.S. Pat. No. 4,424,833, which is mounted to exposed end 22 of sheath 12 for receipt of, and cooperative and usually sealed engagement with, catheters and other medical instruments and devices employed during the medical procedure.

Once the medical procedure is completed, it is necessary to seal puncture 17 through which sheath assembly 10 extends. The procedure or method of the present invention includes as a first step, aligning elongated guide means with the puncture site, which guide means extends from the puncture site through overlying tissue 14.

The aligning step can be accomplished during insertion of sheath assembly 10 into puncture 17, if the sheath assembly is employed as the guide means. Most preferably, however, a guide means, such as guide wire 28 used in the Seldinger technique, can be reinserted into sheath assembly 10 after removal of the medical device used in the invasive procedure. In either case, an elongated guide wire 28 or elongated sheath member 12, which is now also a guide member, is positively axially aligned with the central longitudinal axis of puncture opening 17. The guide means preferably, but not necessarily, extends through puncture 17 to provide positive alignment.

Figure 2:
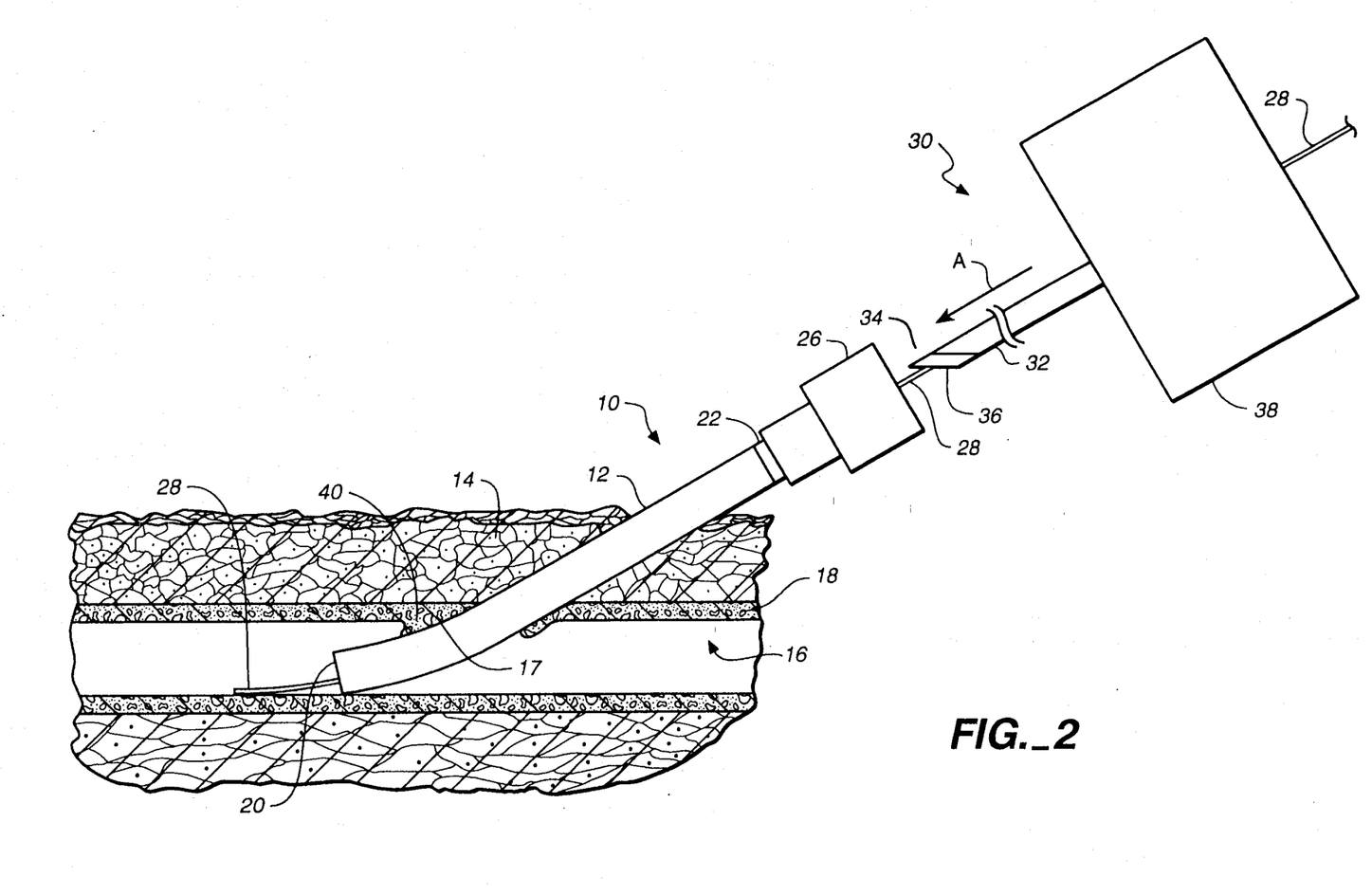
FIG. 2 is a reduced, schematic, side elevation view illustrating insertion of a sealing assembly through the sheath assembly and into a blood vessel in accordance with a preferred embodiment of the invention.

As best may be seen in FIG. 2, in the preferred embodiment of the method of the present invention, a sealing assembly, generally designated 30, is mounted over guide wire 28 and moved in the direction of arrow A down the guide wire and through sealing assembly 26 into sheath member 12. In the preferred embodiment, sealing assembly 30 is an electrosurgical device suitable to effect cauterization or coagulation and including an elongated tubular member 32 which carries one of a heating or coagulating assembly 34 on its annular end. The preferred sealing assembly will be described in more detail in connection with FIG. 6.

The next step in the method of the present invention is the step of moving at least one of the guide means and a sealing assembly axially relative to the other and to puncture 17 until a transversely extending shoulder on at least one of the guide means and sealing assembly encounters increased resistance to movement as a result of substantially direct engagement of the shoulder with wall 18 of the blood vessel. Thus, as is preferred and shown in FIGS. 1-5, sealing assembly 30 and sheath 12 are withdrawn or moved together axially on guide wire 28 until a transverse shoulder thereon is guided into substantially direct engagement with wall 18 around puncture 17.

Since there are numerous brands and lengths of sheath assemblies 10 commercially distributed, FIGS.

1–5 illustrate a sealing assembly 30 in which tubular elongated member 32 has been provided with a length greater than the length of tubular sheath member 12. Thus, annular distal end 36 of member 32 will extend beyond annular distal end 20 of sheath member 12.

Figure 3:
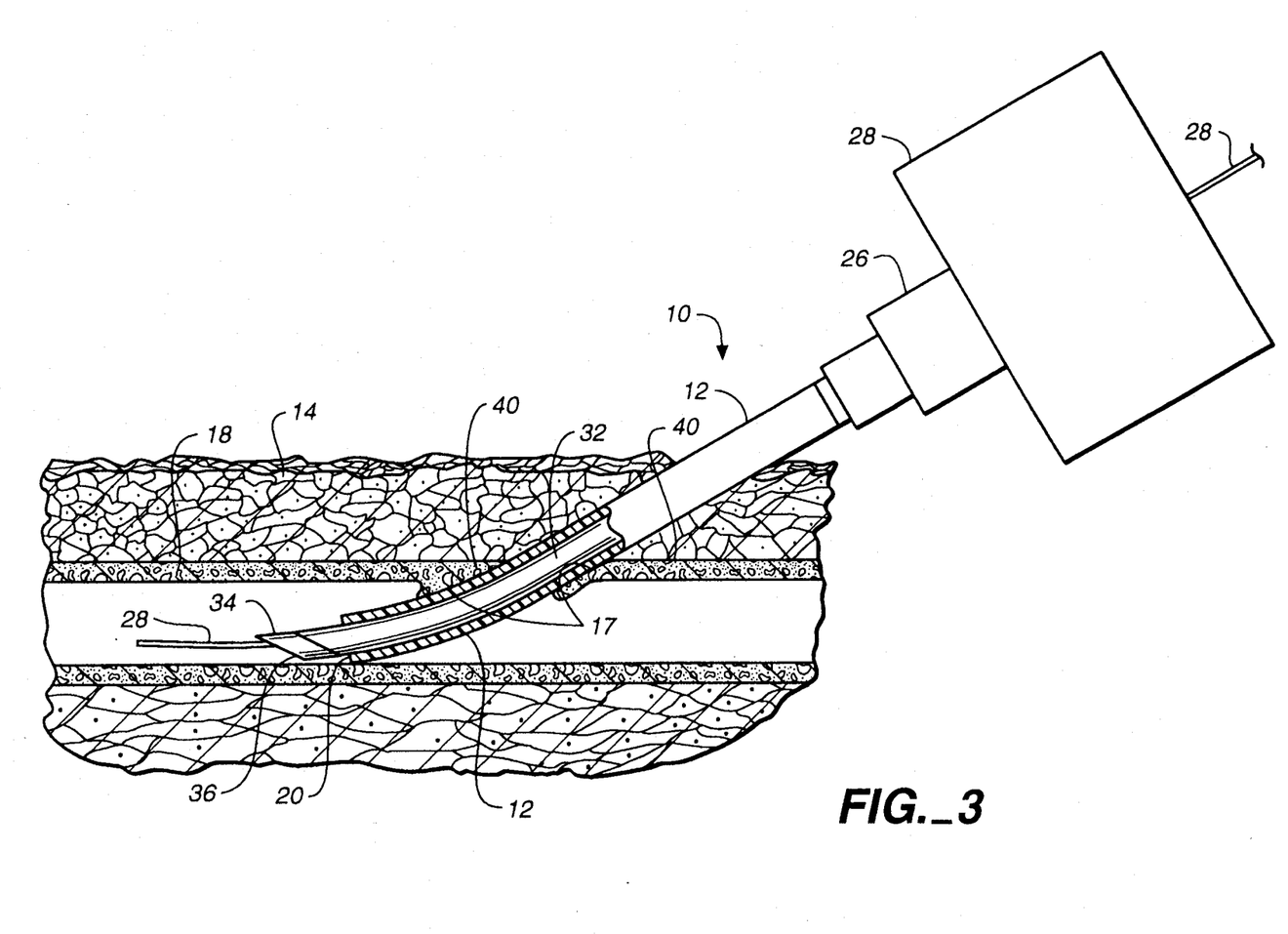
FIG. 3 is an enlarged, schematic, side elevation view of the sealing assembly of FIG. 2 positioned in the blood vessel through the sheath assembly.
Figure 3A:
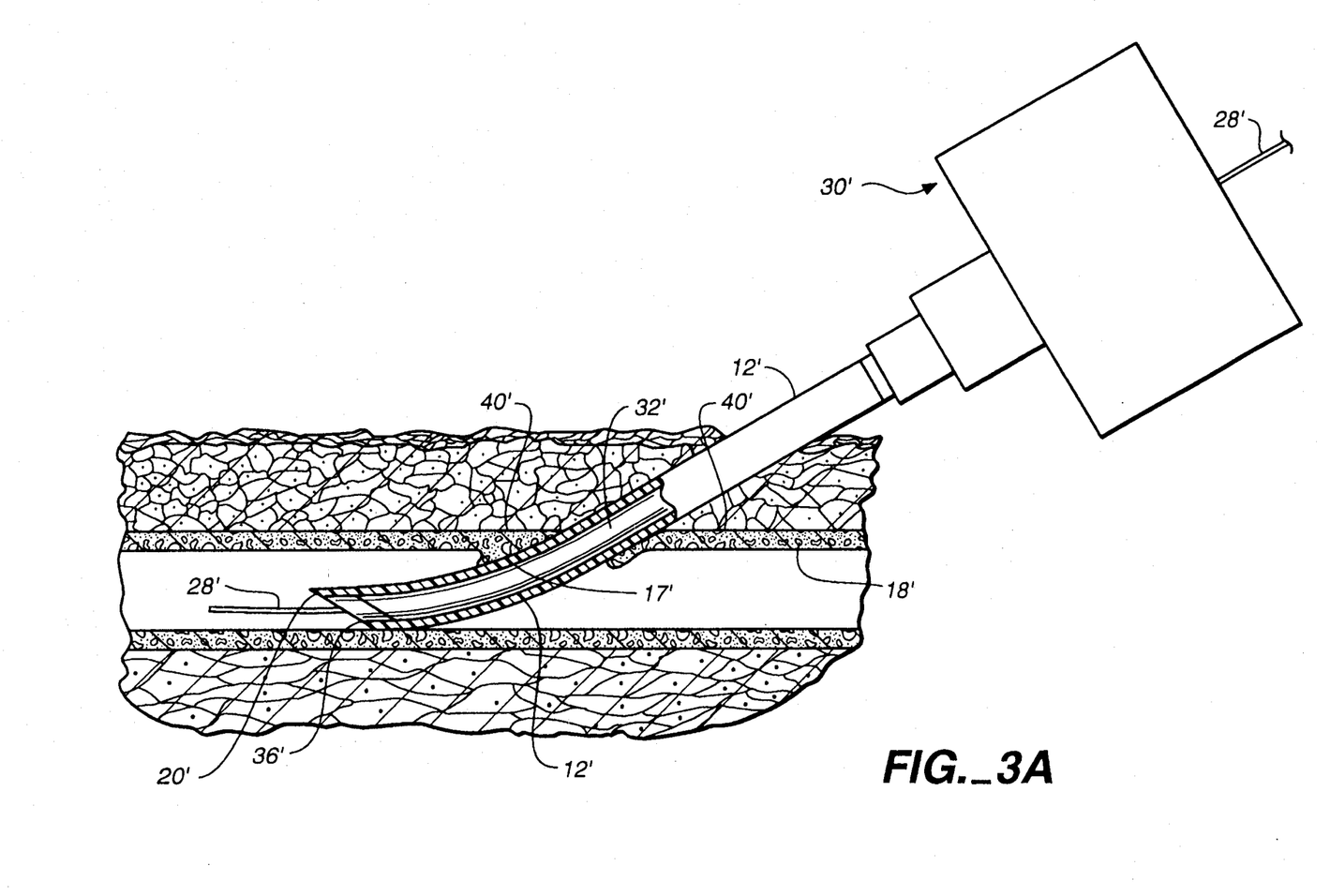
FIG. 3A and FIG. 3B are side elevation views corresponding to FIG. 3 and illustrating alternative sheath and sealing assembly configurations.
Figure 3B:
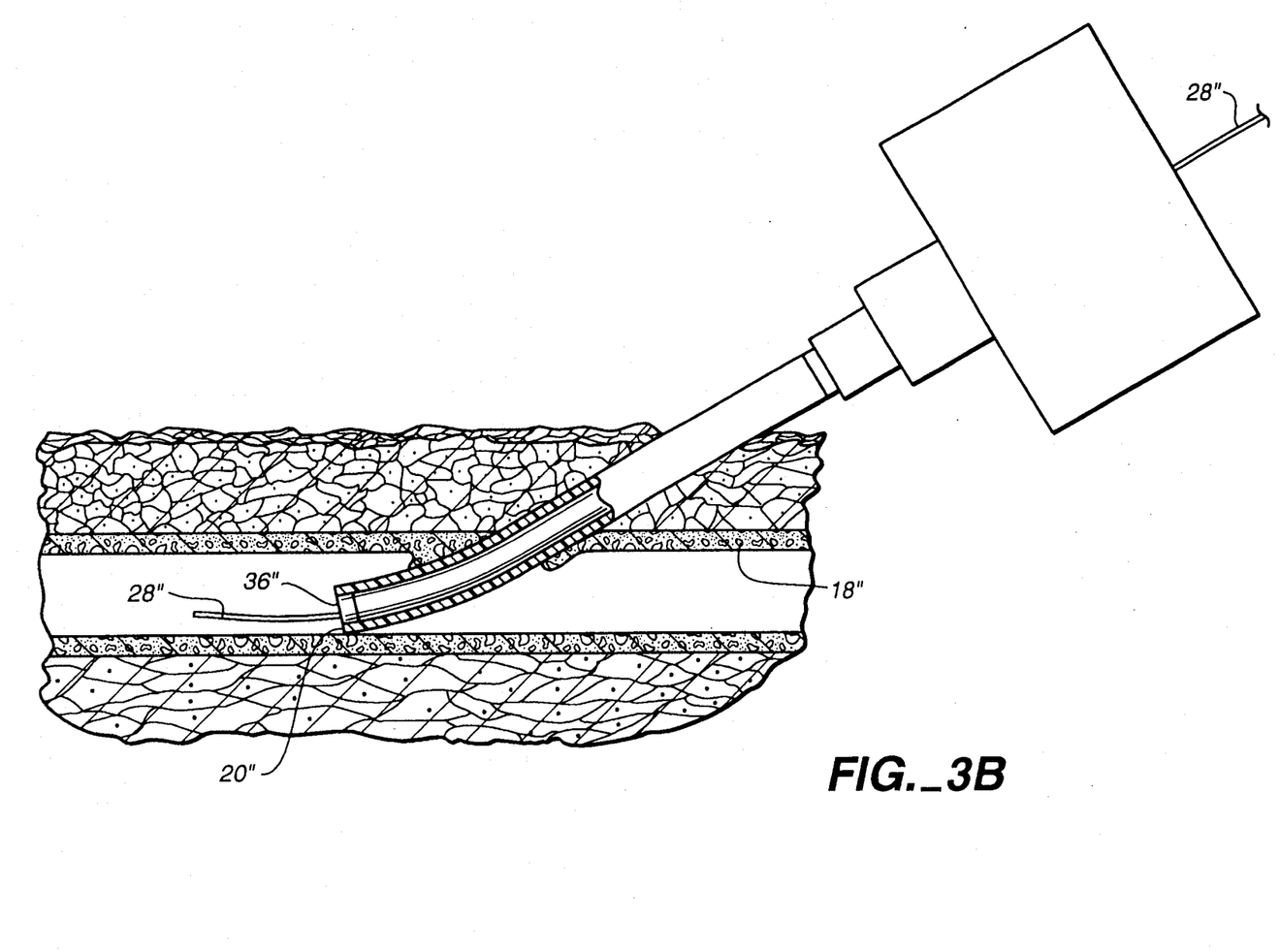

Conventional sheath assemblies 10 are provided with relatively thin-walled, tubular sheath members 12. Thus, in the preferred method of the present invention positive location of the exterior surface 40 of blood vessel 18 surrounding puncture 17 is accomplished using annular end wall 36 of sealing assembly 30 as the transversely extending shoulder. As is described below, a specialized thick-walled sheath member 12 would also enable use of the sheath assembly end wall 20 as a shoulder to locate surface 40, and if the sealing member 32 and sheath have the same length, as shown in FIGS. 3A and 3B, a combination of end walls 36 and 20 can be employed.

Figure 4:
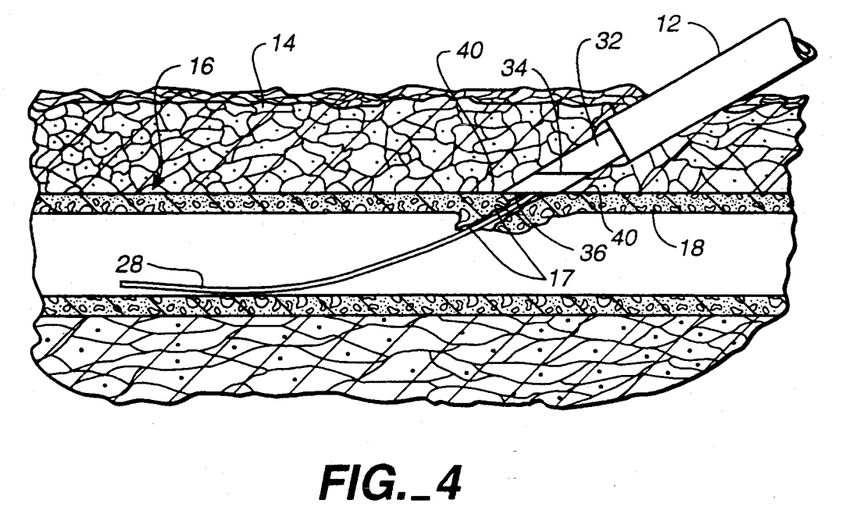
FIG. 4 is an enlarged, schematic side elevation view of the sheath assembly and sealing assembly of FIG. 3, as withdrawn from the blood vessel for sealing of the puncture site.

The preferred method of moving sealing means and the sheath into engagement with surface 40 is to move sheath 12 and sealing means 30 together relative to guide wire 28, namely, by slowly withdrawing sheath 12 and sealing member 32 from a position inside puncture 17 (FIG. 3) along wire 28 to a position outside puncture 17 (FIG. 4).

When the annular end 36 of tubular sealing means 32 is withdrawn from puncture 17, at least one of two phenomena will occur. First, for most blood vessels, wall 18 will be sufficiently resilient that withdrawal of sheath 12 and sealing member 32 will cause resilient contraction of wall 18 at puncture 17 down around guide wire 28. Second, even when blood vessel walls 18 are not very resilient and contract only slightly, if at all, removal of sheath 12 and sealing member 32 automatically will result in guide wire 28, which has a transverse dimension substantially less than the distended puncture opening, being laterally displaced from the center of puncture opening 17 to proximate one side of the puncture. Thus, the annular shoulder or end 36 now will be guided along a laterally displaced guide wire 28. In either case, movement of the sealing assembly and sheath, back toward blood vessel 16 will result in shoulder or annular end 36 substantially directly engaging exterior surface 40 of wall 18 at the puncture site. Such engagement of the annular shoulder of the sealing means with wall 18 will result in the occurrence of an increased resistance to movement toward the blood vessel, as compared to the resistance to movement present during withdrawal of the sheath and sealing member.

In the preferred procedure of FIGS. 1–5, therefore, sheath assembly 12 and sealing assembly 30 are slowly withdrawn by a short distance from within puncture 17 and then advanced slightly. This is repeated with slightly larger withdrawal distances than advancement distances until withdrawal from the blood vessel occurs and an increased resistance can be felt or sensed on the next advance toward the blood vessel.

As used herein, the expressions "substantially direct engagement" and "substantially direct contact" shall include direct abutting contact by end 36 with surface 40 of wall 18 and engagement in which the shoulder is separated from surface 40 of wall 18 only by a very thin layer of tissue 14, for example, a layer substantially less than the thickness of blood vessel wall 18.

Once annular end wall or shoulder 36 of sealing means 30 is brought into substantially direct engagement with wall 18 around puncture 17, the method of the present invention includes the step of sealing puncture 17, most preferably by electro-cauterizing or electro-coagulating blood escaping from contracted puncture 17. It will be understood, however, that other puncture sealing techniques can be employed once sealing means end 36 is positively guided into substantially direct contact with the puncture site.

Figure 5:
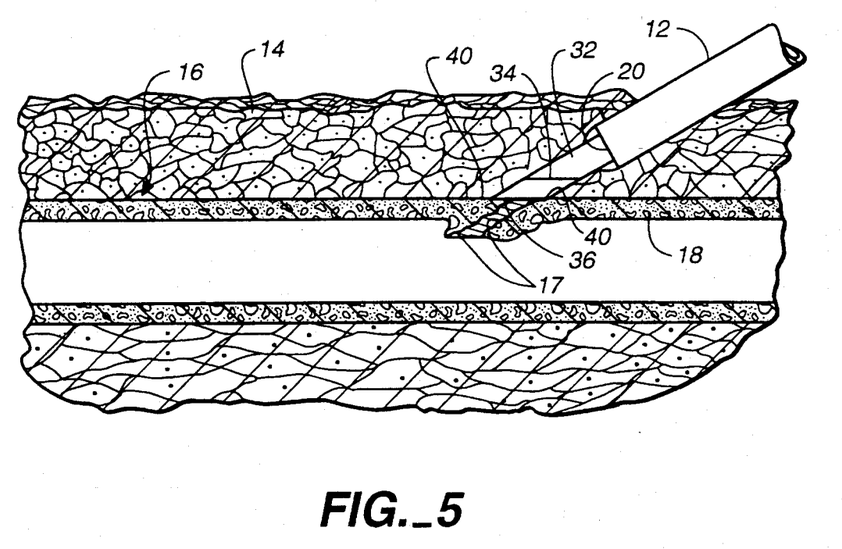
FIG. 5 is a schematic, side elevation view illustrating withdrawal of the guide wire from the blood vessel after partial heat cauterization.

As may be seen from FIGS. 4 and 5, electrosurgical sealing preferably is a two step procedure in which most of the area of puncture 17 is heat cauterized or coagulated, while guide wire 28 extends through puncture 17 (FIG. 4). The area of guide wire 28 is next heat cauterized or electro-coagulated after removal of guide wire 28, as shown in FIG. 5. It should be noted that the substantially direct engagement of the puncture site by shoulder or end 36 during electrosurgical sealing also tamponades the puncture site to aid the hemostasis process. After removal of wire 28 and sealing of the guide wire opening, sheath assembly 10 and sealing assembly 30 can be withdrawn together from tissue 14.

In order to provide the maximum shoulder dimension for location of surface 40 around puncture 17, sheath assembly 10 and sealing assembly 30 ideally have lengths and end configurations which are matched or can be manipulated until the ends are substantially coplanar. As may be seen in FIG. 3A, therefore, end 20' of sheath member 12' and end 36' of sealing assembly 30' are coplanar and oriented at an angle to guide wire 28' to engage surface 40' proximate puncture 17' at an angle close to parallel to blood vessel wall 18'. When the combined annular shoulder comprised of annular walls 20' and 36' are withdrawn from opening 17' the next advance of the sheath and sealing means toward the blood vessel will be met with a substantial increase in resistance.

In FIG. 3B, ends 20" and 36" again are substantially coplanar, but they are oriented at about ninety degrees to guide wire 28". Thus, they present a large combined shoulder, but the shoulder is not substantially parallel to blood vessel wall 18".

Guided movement of a shoulder into substantially direct contact with blood vessel 16 can be accomplished using other manipulation techniques. Thus, as may be seen from FIG. 7, puncture-distending sheath assembly 10 has been used to reintroduce guide wire 28a into blood vessel 16a through puncture 17a. The sheath assembly has been removed from blood vessel 16a and tissue 14a, leaving guide wire 28a in place. A sealing assembly 30a, having elongated tubular sealing member 32a, is then mounted over guide wire 28a and advanced slowly in the direction of arrow B toward puncture 17a. In order to insure location of the exterior surface 40a of blood vessel wall 18a, sealing assembly member 32a can have a diameter which is greater than the diameter of the removed sheath assembly. For example, if the sheath assembly had a diameter of 8 French, member 32a may have a diameter of 10 or 12 French.

Figure 7:
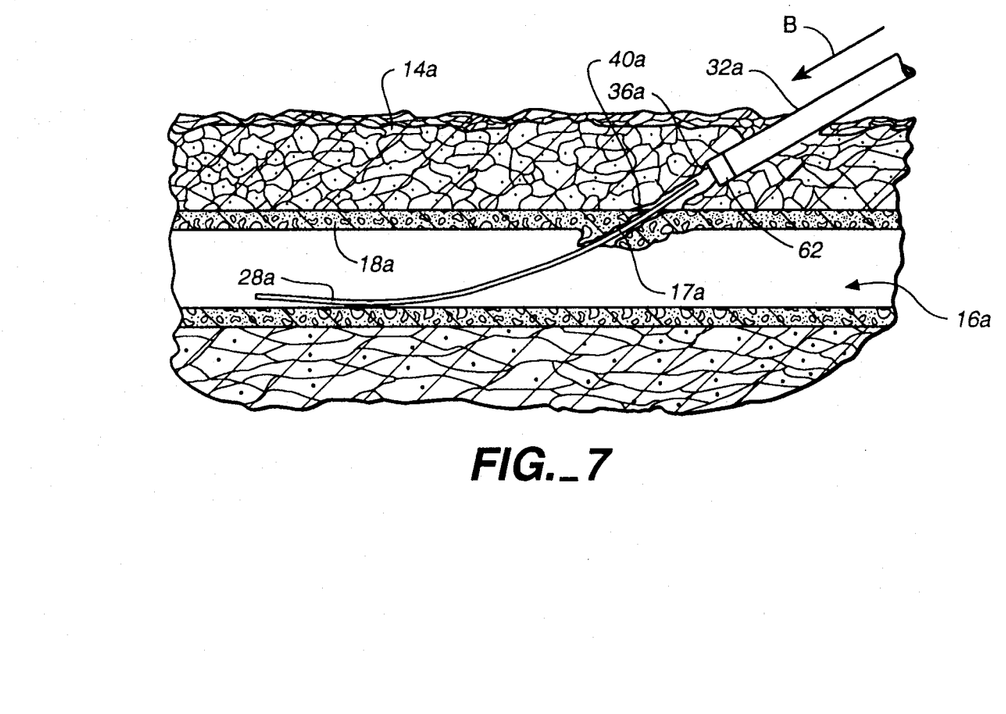
FIG. 7 is a schematic, side elevation view illustrating an alternative embodiment of the apparatus and method of the present invention.

When sealing member end shoulder 36a reaches the contracted wall 18a at puncture site 17a, or is guided by laterally shifted wire 28a into contact with surface 40a of wall 18a, increased resistance to advancement will be sensed by the doctor, indicating that end 36a is in substantially direct engagement with the puncture site. Electrosurgical or other forms of sealing then can proceed as above described.

Figure 9:
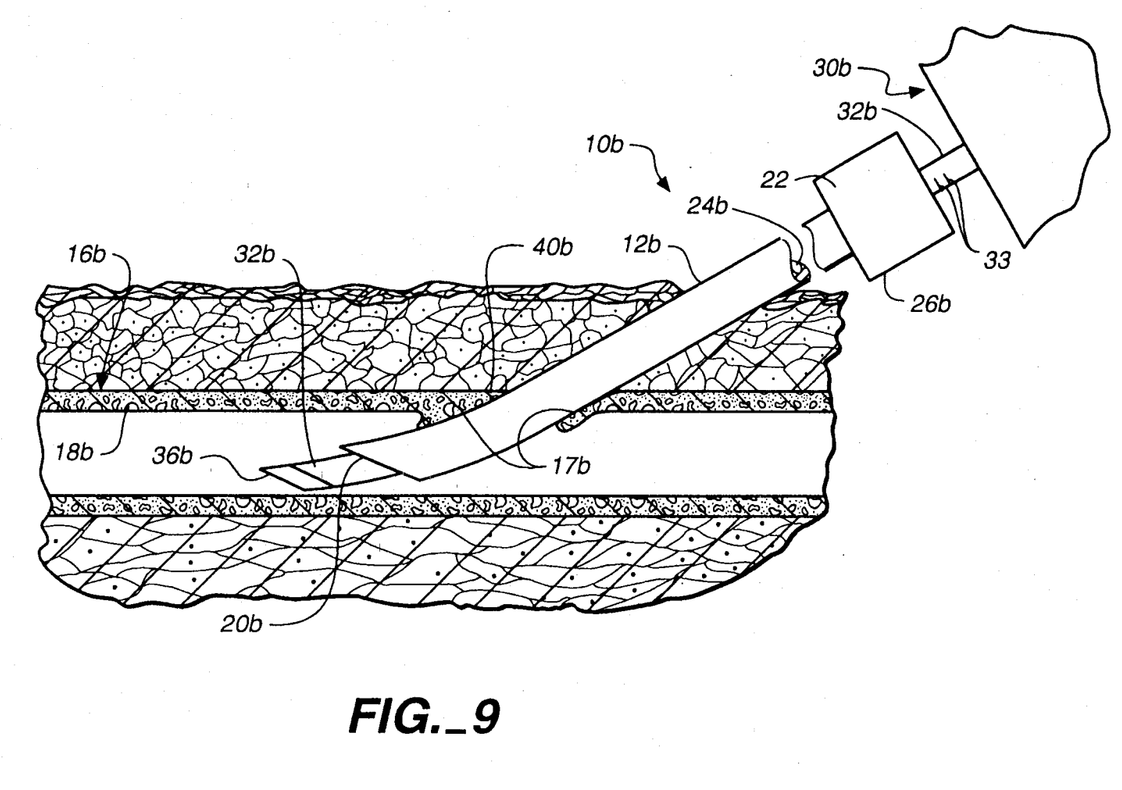
FIG. 9 is a schematic, side elevation view corresponding to FIG. 7 illustrating still a further embodiment of the method of the present invention.

In the procedure illustrated in FIG. 9, the instrument or device used in the medical procedure is first removed from sheath assembly 10b. Since the puncture-distending sheath member usually is a relatively thin-walled member, it is preferable that the original sheath be replaced by a sheath member 12b having a relatively thick wall so that the annular shoulder 20b has sufficient transverse dimension to be used to locate surface 40b surrounding puncture. Elongated member 32b of sealing means 30b is then introduced and guided down lumen 24b until end 36b is inside blood vessel 16b to align the sealing assembly with the longitudinal axis of puncture 17b.

In the procedure of FIG. 9, sheath assembly 10b is now slowly withdrawn, preferably by short reciprocating cycles in which the sheath is first withdrawn and then advanced on sealing member 32b, which now acts to guide sheath 12b. The withdrawal portion of each cycle should be slightly greater in distance than the advancement portion so that annular end shoulder 20b of the sheath will eventually be withdrawn from wall 18b. Once end 20b is withdrawn, the next advancement step will cause it to be advanced against the contracted wall or side of puncture 17b toward which member 32b is automatically laterally displaced when sheath 12b clears puncture 17b.

The result is that the doctor can feel when shoulder 20b is withdrawn from the puncture and then advanced back against exterior surface 40b of wall 18b. When increased resistance to advancement of sheath 12b is felt, transverse shoulder 20b will be in substantially direct contact with the puncture site, and sealing member 32b has positively maintained the alignment of the sheath during location of the wall surrounding the puncture site. Now, sealing assembly 30b can be moved slowly out of puncture 17b until end 36b of the sealing tip is proximate annular sheath shoulder 20b. This can be facilitated, for example, by placing indicia, such as lines 33 on outer end of sealing member 32b. The first of lines 33 may indicate, for example, that end 36b is one or two millimeters from end 20b and the next line 33 can indicate that the two ends are coplanar. It will be seen from FIG. 9 that sheath end 20b is optionally formed to be inclined in a manner similar to end 36b of the sealing assembly so that both will mate with or be more closely aligned with surface 40b.

Electrosurgical or other sealing can begin, for example, at the first of the two lines 33 and proceed as the sealing member 32b is withdrawn inside sheath 12b to the second of lines 33. Additional lines 33 can be provided as desired. The sealing tip 36b of sealing assembly 30b can be a solid or unperforated tip since no guide wire is required for this procedure. Unperforated end 36b also aids in its tamponade-effect during hemostasis.

The method described in connection with FIG. 9 may be somewhat less desirable than the method of FIGS. 1-5, 3A, 3B and 7 in that the shoulder 20b provided by sheath 12b will not be as large as the annular shoulders 36, 20' and 36', 20" and 36" and 36a. In the FIG. 9 procedure the sealing means maintains positive alignment as cauterization starts and is withdrawn as it ends.

It also may be possible to use the original thin-walled sheath and still sense the blood vessel wall upon withdrawal along sealing means 30b, but substitution of a thick-walled sheath 12b will facilitate tactile sensing of the increased resistance.

Figure 10:
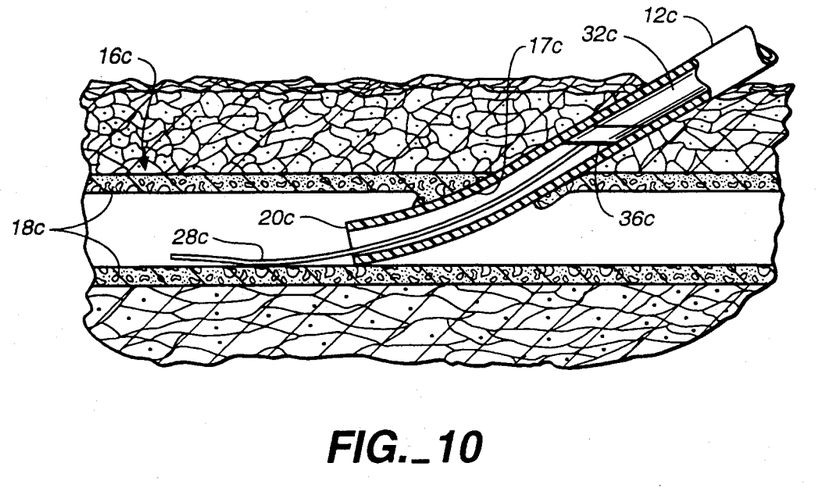
FIG. 10 is a schematic, side elevation view of an alternative embodiment of the subject sealing assembly positioned through a sheath assembly and into a blood vessel.

Still a further embodiment of the procedure of the present invention can be described by reference to FIG. 10. Sheath 12c is again left in place and a sealing member 32c and guide wire 28c and inserted down the sheath. In this procedure sealing end 36c does not extend from end 20c of the sheath, but guide wire 28c does.

Sheath 12c is withdrawn from puncture 17c in wall 18c by a reciprocating technique until annular sheath shoulder 20c is removed from wall 18c and then advanced back against the contracted puncture 17c and/or a side of the puncture as a result of lateral shifting guide wire 28c. Once the outside of blood vessel 16c has been located at the puncture site, and alignment is maintained by wire 28c, sealing member 32c may be advanced down sheath 12c until end 36c is substantially directly engaged with blood vessel wall 18c at puncture 17c. Sealing may then proceed as described in connection with FIGS. 1-5.

Figure 11:
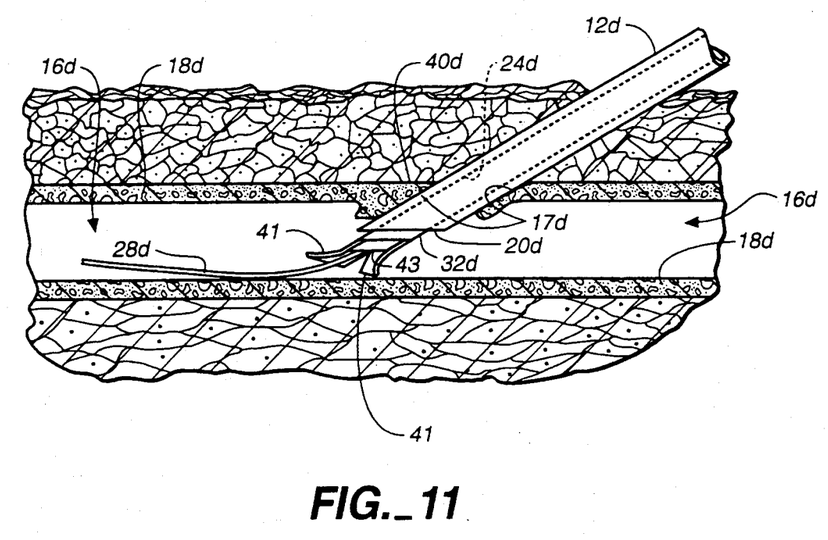
FIG. 11 is a schematic, side elevation view of the subject sealing assembly being inserted through overlying tissue to a blood vessel wall in accordance with still another alternative embodiment of the method of the present invention.

In FIG. 11 still a further alternative embodiment is illustrated in which sealing assembly 30d includes an expansible end 36d to even more positively locate the outside surface 40d of wall 18d around puncture 17d. End 36d can include a plurality of radially expansible finger 41 which are maintained in a radially confined condition for passage down lumen 24d of sheath 12d. Fingers 41 can be loaded into the outer end of the sheath by a loading collar (not shown) which allows the fingers to be slid into lumen 24d in a contracted condition. When end 36d passes inwardly of end 20d of the sheath, fingers 41 are free to radially expand, as shown in FIG. 11, preferably to a diameter larger than the sheath diameter. The sheath and sealing member may then be withdrawn using a reciprocation technique until resilient fingers 41 pass beyond wall 18d. Wire 28d maintains positive alignment and fingers 41 provide a shoulder assembly that is very positive in percutaneously locating the outside of wall 18d.

A sealing end can be located inside fingers 41 and the sealing assembly urged against blood vessel 16d until the fingers separate by an amount causing annular end surface 43 to be in substantially direct contact with wall 18d for electrosurgical or other sealing techniques.

Sealing assemblies 30-30d preferably are electrosurgical sealing assemblies such as resistance heating or electro-coagulating sealing assemblies of the general type as are currently in use in non-percutaneous procedures. Thus, an electro-coagulating device is marketed under the trademark BOVIE which uses currents, voltages and frequencies to coagulate blood escaping from blood vessels. This device has a remote or floor-supported electrosurgical current generator constructed, for example, as set forth in U.S. Pat. Nos. 3,699,967, 3,801,800 and 3,963,030, which is electrically connected to the hand-manipulated instrument. The instrument, however, has a relatively short and wide coagulating tip, and it would not be suitable for use in the percutaneous procedure of the present invention without modification to provide an elongated narrow wand-like member 32-32e. Otherwise, however, the power controls and other components are suitable for use in the present invention.

Additionally, a batter-powered electro-cautery device is also being commercially exploited under the trademark ACUTEMP SURGICAL by Concept, Inc. of Largo, Fla. This device also is the subject of U.S. Pat. No. 3,613,682, and as modified to have an elongated tubular or rod-like members 32-32d formed for cooperative or sliding movement along guide means, such a battery-powered device would be preferable for use in the process and apparatus of the present invention.

Figure 6:
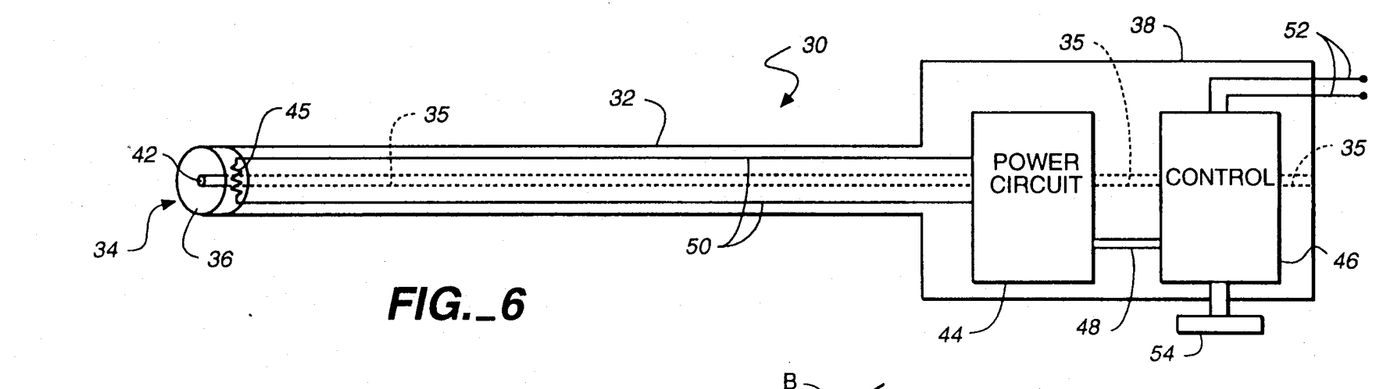
FIG. 6 is a schematic, bottom plan view of a sealing assembly constructed in accordance with a preferred embodiment of the invention.

Referring to FIG. 6, sealing assembly 30 generally includes a narrow, elongated member 32, a sealing assembly 34 with a resistance heating or electro-coagulation element 45 mounted proximate distal end 36 of member 32, and an energy source assembly 38 connected to element 45 to enable application of sufficient energy to the puncture site to effect hemostasis. Elongated member 32 of sealing assembly 30 may be flexible and conform to any curvature of sheath 12 through tissue 14. Alternatively member 32 and sheath 12 can be relatively inflexible and enter blood vessel 16 along a substantially straight line.

When heating assembly 34 is in firm, substantially direct contact with the external surface of the blood vessel wall, energy source 38 is activated to deliver energy to sealing element 45. Sealing element 45 then cauterizes or coagulates blood at the puncture site, creating a vascular seal to stanch the flow of blood from the operative blood vessel. During the sealing process, sheath 12 also serves as an insulator, permitting energy to be delivered primarily to vessel wall 18 and reducing the transfer of energy to overlying tissue 14.

Elongated sealing member 32 preferably is tubular having a lumen 35 for receiving guide wire 28 therethrough. Sealing member 36b, however, is solid and does not require the use of a guide wire. Sealing assembly lumen 35 preferably extends completely through the entire instrument so that the sealing assembly can be easily mounted on guide wire 28, however, a side exit (not shown) can be provided in the outer end of member 32 to allow insertion of the guide wire without going through the power source assembly 38. Shaft 32 also is formed for cooperative engagement with lumen 24 of sheath assembly 10. In a preferred embodiment, both shaft 32 and sheath 10 are cylindrical in shape so that shaft 32 may be slidably inserted through inner lumen 24 of sheath 12 and into an operative blood vessel.

The sealing tip 36 may be oriented at a substantially right angle with respect to the longitudinal axis of cylindrical shaft 32, as seen in FIGS. 3B and 7. Alternatively, the tip may be inclined with respect to the longitudinal axis of shaft 32, as shown in FIGS. 3A and 2-5, to provide a more effectively oriented contact surface with respect to blood vessel wall. As seen most clearly in FIG. 4, when sealing assembly 30 is withdrawn from blood vessel 16, the sealing element 34 is oriented approximately parallel to exterior surface 40 of blood vessel wall 18. In this embodiment, the tip is preferably inclined at the same angle as the angle of entry of sealing assembly 30 through the patient's skin, which is about a 30° to about 60° angle.

Energy source assembly 38 may include a power circuit 44, which for an electro-cautery device can include a battery, and a control device 46, such as a rheostat, electrically coupled to power circuit 44 via conductor means 48. In a preferred embodiment, power circuit 44 communicates with the electro-cautery tip via leads 50 to communicate electricity to resistance heater 45 at the tip. Power circuit 44 also may be connected through control 46 to an outside energy source (not shown) via connector leads 52. Control 46 is coupled to and is responsive to an operator input element 54. A physician may control parameter characteristics, such as the amount of heat and the duration of heat, by input means such as element 54, and control 46 receives the input and communicates the same to power circuit 44. Power circuit 44 then causes the necessary electrical energy to flow to resistance heater 45 to heat cauterize the puncture site. Battery-powered implementation of an electro-coagulation embodiment also may be feasible.

Figure 8:
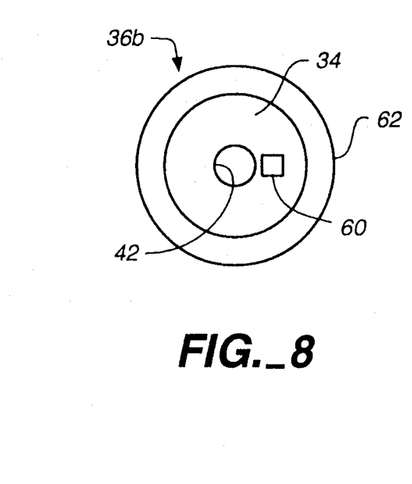
FIG. 8 is an enlarged, end view of the electrosurgical tip on the distal end of the sealing assembly of FIG. 7.

In another aspect of the invention, an electro-cautery sealing assembly 34 also may include sensor 60 (FIG. 8) for sensing the temperature at the puncture site. In this particular embodiment, the sensor electrically communicates with power circuit 44 to enable the generation of the correct amount of thermal energy based on the temperature sensed at the vessel wall. Tip assembly 36b in FIG. 8 also may include an annular thermally insulative portion 62 surrounding heating element assembly 43. Insulation portion 62 serves to limit thermal injury to healthy tissue surrounding the puncture site and better enables identification of vessel wall surface 40 by providing a tip with an increased surface area. Insulation portion 62 also contributes to the tamponading of the blood flow from the puncture, as the electro-cautery tip is brought into contact with and is advanced toward vessel wall surface 40.

In describing the invention, reference has been made to a preferred embodiment and illustrative advantages of the invention. Those skilled in the art, however, and familiar with the instant disclosure of the subject invention, will recognize additions, deletions, modifications, substitutions, and other changes which will fall within the purview of the subject invention and claims.

What is claimed is:

1. A percutaneous procedure for positioning a vascular sealing assembly to enable percutaneous sealing of a puncture opening at a puncture site in a blood vessel comprising the steps of:

aligning an elongated guide in axial alignment with the puncture opening, said guide extending from the puncture opening through tissue overlying the blood vessel to an exterior thereof;

mounting said sealing assembly to said guide for guided movement therealong; and inserting said sealing assembly into the blood vessel through the puncture site and reciprocating said sealing assembly by moving said sealing assembly in a rearward direction and then in a forward direction along said guide in sufficiently small increments to detect substantially direct engagement of a shoulder on said sealing assembly with an exterior surface of a wall of the blood vessel surrounding the puncture opening as said sealing assembly is withdrawn from the puncture site.

2. A procedure for percutaneously sealing a puncture opening at a puncture site in a wall of a blood vessel comprising the steps of:

positioning a guide to extend through tissue overlying the blood vessel and into and through the puncture opening to establish a positive alignment of said guide with the puncture opening;

mounting a sealing assembly to said guide for movement with respect thereto and moving said sealing assembly through the tissue along said guide to the blood vessel;

inserting said sealing assembly into the blood vessel through the puncture site and then incrementally withdrawing and advancing said sealing assembly along said guide until increased resistance is encountered upon advancement of said sealing assembly indicating a shoulder of said sealing assembly is in substantially direct contact with the wall surrounding the puncture opening; and thereafter percutaneously sealing the puncture opening while maintaining said sealing means aligned with the puncture opening and in substantially direct engagement with the wall of the blood vessel.

3. A percutaneous procedure as defined in claim 2 wherein,
said positioning step is accomplished by positioning a guide in the form of an elongated sheath assembly through the puncture site; and
said withdrawing and advancing step is accomplished by incrementally withdrawing and then advancing said sheath assembly until said increased resistance is encountered upon advancement.

4. A percutaneous procedure as defined in claim 2 wherein,
said sealing step is accomplished by applying sufficient heat to the puncture site to effect heat cauterization of the puncture site.

5. A percutaneous procedure as defined in claim 4, and further comprising the step of:
during said sealing step, substantially directly contacting the blood vessel with said sealing assembly to apply pressure thereto during the application of heat.

6. A percutaneous procedure as defined in claim 5 wherein,
during said sealing step, withdrawing said guide from alignment with the puncture site.

7. A percutaneous procedure as defined in claim 2 wherein,
said sealing step is accomplished by applying a coagulating current, voltage and frequency to the puncture site.

8. A method of obtaining a percutaneous vascular seal at a puncture site in a blood vessel comprising the steps of:
positioning a percutaneous vascular sealing assembly having electrosurgical sealing means carried thereon inside the blood vessel through a puncture opening at the puncture site;
withdrawing said sealing assembly from the blood vessel until said electrosurgical sealing means can be sensed to be positioned substantially in direct contact with an exterior wall of the blood vessel at the puncture site; and
applying one of sufficient heat and sufficient coagulating current to blood escaping the blood vessel while said electrosurgical sealing means is substantially in direct contact with the exterior surface of the blood vessel to effect hemostasis of the puncture opening.

9. A method of obtaining a vascular seal as defined in claim 8 and further comprising the step of:
prior to said positioning step, inserting a guide wire through the puncture opening; and
during said withdrawing step, moving said sealing assembly along said guide wire.

10. A method of obtaining a vascular seal as defined in claim 9 wherein,
said inserting step is accomplished by slidably inserting said sealing assembly through an inner channel of a sheath assembly extending along said guide wire and into the blood vessel.

11. A method of obtaining a vascular seal as defined in claim 10 wherein,
said withdrawing step is accomplished by simultaneously withdrawing said sheath assembly and said sealing assembly along said guide wire by a small distance, and then advancing said sheath assembly and said sealing assembly along said guide wire by a distance less than the distance moved during said withdrawing step, and repeating said withdrawing step and said advancing step until increased resistance is encountered during said advancing step.

12. A method of obtaining a vascular seal as defined in claim 9 further comprising the step of:
after said applying step, removing said guide wire from the puncture site and applying more sealing energy to the puncture site to seal the opening left by said guide wire.

13. A percutaneous procedure for positioning a vascular sealing assembly to enable percutaneous sealing of a puncture opening at a puncture site in a blood vessel comprising the steps of:
inserting an elongated guide wire into the puncture opening, said guide wire extending from the puncture opening through tissue overlying the blood vessel to an exterior thereof;
mounting a tubular electrosurgical sealing device having a lumen dimensioned for sliding engagement with said guide wire onto said guide wire, said sealing device having a sealing surface transversely oriented relative to said guide wire with a dimension greater than the transverse dimension of the puncture opening; and
manually manipulating said sealing device axially on said guide wire until said sealing surface can be felt to engage an exterior surface of a wall of the blood vessel surrounding the puncture opening.

14. A percutaneous procedure as defined in claim 13 wherein,
prior to said manually manipulating step, withdrawing a puncture opening distending sheath assembly positioned in said puncture opening from the blood vessel; and
during said manually manipulating step, manipulating said sealing device along said guide wire until said sealing surface on said sealing device substantially directly engages a resiliently contracted blood vessel wall at the puncture site.

15. A percutaneous procedure as defined in claim 13 wherein,
said inserting step is accomplished by inserting said guide wire having a transverse dimension less than the puncture opening enabling lateral displacement of said guide wire to a position proximate one side of the puncture opening; and
during said manually manipulating step, manipulating said sealing device until said guide wire is free for lateral displacement and said surface on said sealing device substantially directly engages the blood vessel at said one side of the puncture opening.

16. A percutaneous procedure as defined in claim 13 which further includes:
after said manually manipulating step, electrosurgically sealing the puncture site.

17. A percutaneous procedure as defined in claim 16 wherein,
said electrosurgically sealing step is accomplished by electro-cauterizing the puncture site with a heat cauterization device.

18. A percutaneous procedure as defined in claim 16 wherein, said electrosurgically sealing step is accomplished by electro-coagulating the puncture site with an electro-coagulating device.

19. A percutaneous procedure as defined in claim 13 wherein, said inserting step is accomplished by positioning a tubular sheath having a lumen therethrough in the puncture opening at the puncture site by inserting said guide wire through said lumen, and said manually manipulating step is accomplished by inserting said sealing device into said lumen of said sheath along said guide wire and into the blood vessel.

20. A percutaneous procedure as defined in claim 19 wherein, said manually manipulating step is accomplished by simultaneous withdrawal of said sealing device and said sheath from the puncture opening along said guide wire.

* * * * *